United States Patent [19]
Markin

[11] Patent Number: 5,427,743
[45] Date of Patent: Jun. 27, 1995

[54] SPECIMEN CARRIER

[75] Inventor: Rodney S. Markin, Omaha, Nebr.

[73] Assignee: Board of Regents - Univ. of Nebraska, Lincoln, Nebr.

[21] Appl. No.: 193,734

[22] Filed: Feb. 9, 1994

Related U.S. Application Data

[63] Continuation-in-part of Ser. No. 62,785, May 14, 1993.
[51] Int. Cl.⁶ .................................................. B01L 9/06
[52] U.S. Cl. .................................. 422/104; 422/64; 422/102; 206/446; 206/459.5; 211/74; 211/194
[58] Field of Search .................. 422/102, 104, 64, 65; 206/446, 443, 459.5; 211/194, 74

[56] References Cited

U.S. PATENT DOCUMENTS

| | | | |
|---|---|---|---|
| 3,713,771 | 1/1973 | Taylor et al. | 422/104 |
| 3,724,654 | 4/1973 | Gerard et al. | 206/459 |
| 3,897,216 | 7/1975 | Jones | 422/104 |
| 3,916,157 | 10/1975 | Roulette et al. | 235/61.12 R |
| 4,022,579 | 5/1977 | Revillit et al. | 422/104 |
| 4,454,939 | 6/1984 | Kampf et al. | 198/341 |
| 4,484,522 | 11/1984 | Baudisch et al. | 422/104 |
| 4,738,824 | 4/1988 | Takeuchi | 422/63 |
| 4,938,369 | 7/1990 | Carilli | 211/74 |
| 5,021,218 | 6/1991 | Davis et al. | 422/104 |
| 5,069,336 | 12/1991 | Mauthe | 206/219 |
| 5,148,919 | 9/1992 | Rubin | 206/443 |
| 5,217,694 | 6/1993 | Gibler et al. | 422/104 |

*Primary Examiner*—Robert J. Warden
*Assistant Examiner*—N. Bhat
*Attorney, Agent, or Firm*—Zarley, McKee, Thomte, Voorhees & Sease; Mark D. Frederiksen

[57] ABSTRACT

A specimen carrier is designed for transporting specimen tubes throughout an automatic laboratory conveyance system. The specimen carrier includes a generally rectilinear carrier body with a forward face having an identification zone delimited thereon. An identification code is marked in the identification zone so as to permit mechanical sensing and identification of the carrier on a conveyor system. A plurality of holes of various diameters and depths are provided in the top surface of the carrier to receive specimen tubes of various types. The deepest holes are located centrally, so that the carrier is stable while retaining specimens therein. A groove is formed in the top surface of the carrier body which extends between the specimen tube holes, so as to communicate any fluid spilling from a test tube to the other empty holes in the specimen carrier, thereby retaining the fluid within the body of the carrier. A special vertical slot is provided in one of the vertical holes, utilizing a pair of opposing vertical channels, so as to retain a specimen slide in the specimen carrier.

7 Claims, 4 Drawing Sheets

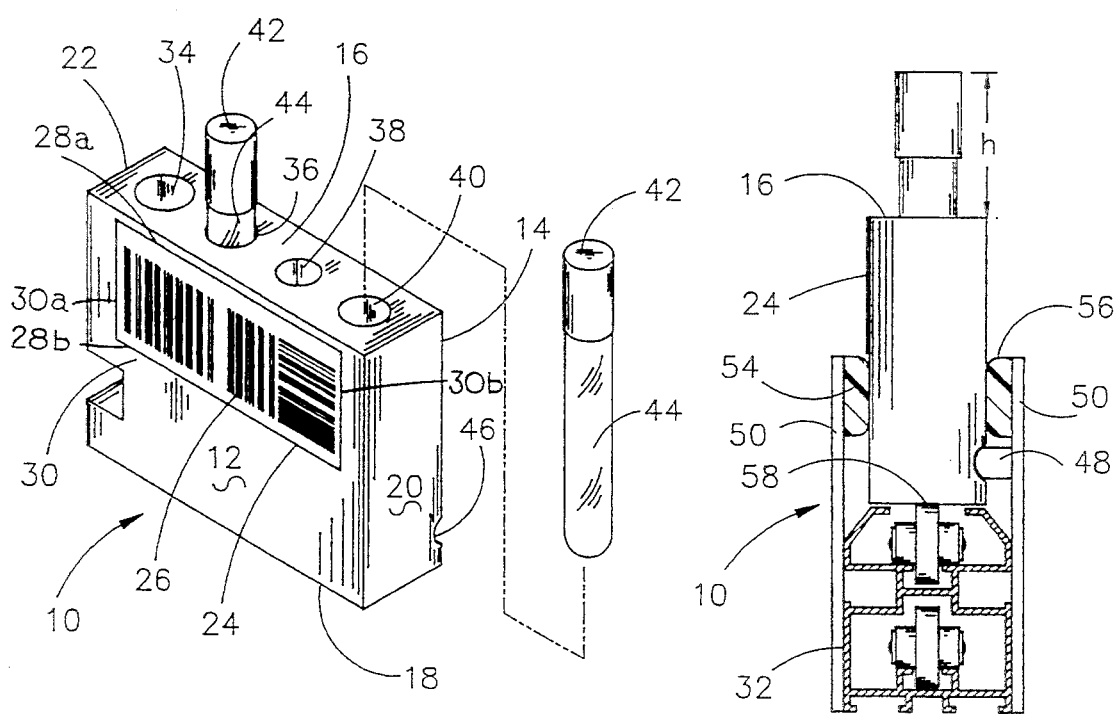
FIG. 1
FIG. 2
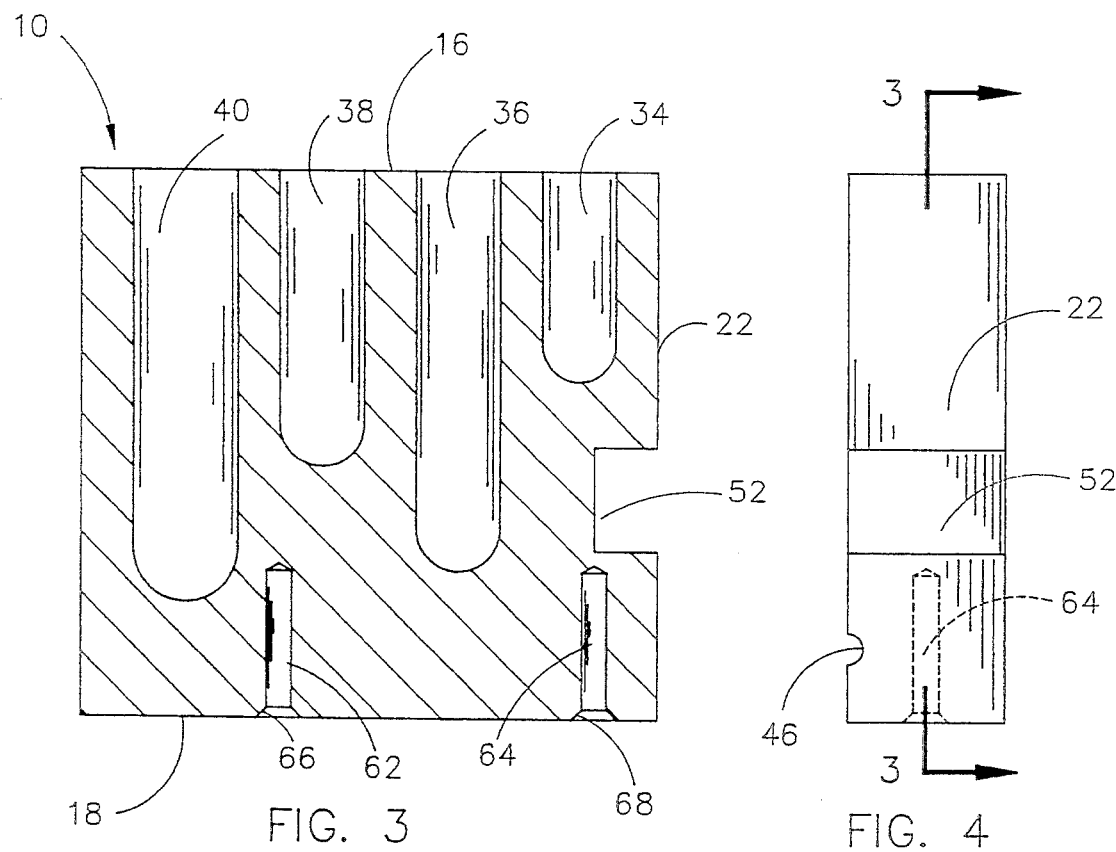
FIG. 3
FIG. 4

SPECIMEN CARRIER

CROSS-REFERENCE TO RELATED APPLICATION

This is a continuation-in-part application of Ser. No. 08/062,785 filed May 14, 1993.

TECHNICAL FIELD

The present invention relates generally to apparatus for carrying laboratory specimens, and more particularly to a carrier for transporting test tubes with specimens therein.

BACKGROUND OF THE INVENTION

Clinical laboratory testing has changed and improved remarkably over the past 70 years. Initially, tests or assays were performed manually, and generally utilized large quantities of serum, blood or other materials/body fluids. As mechanical technology developed in the industrial work place, similar technology was introduced into the clinical laboratory. With the introduction of new technology, methodologies were also improved in an effort to improve the quality of the results produced by the individual instruments, and to minimize the amount of specimen required to perform each test.

More recently, instruments have been developed to increase the efficiency of testing procedures by reducing turnaround time and decreasing the volumes necessary to perform various assays. Present directions in laboratory testing focus on cost containment procedures and instrumentation. Laboratory automation is one area in which cost containment procedures are currently being explored. Robotic engineering has evolved to such a degree that various types of robots have been applied in the clinical laboratory setting.

The main focus of prior art laboratory automation relies on the implementation of conveyor systems to connect areas of a clinical laboratory. Known conveyor systems in the laboratory setting utilize separate conveyor segments to move specimens from a processing station to a specific laboratory work station. In order to obtain cost savings, the specimens are sorted manually, and test tubes carrying the specimens are grouped in a carrier rack to be conveyed to a single specific location. In this way, a carrier will move a group of 5–20 specimens from a processing location to a specific work station for the performance of a single test on each of the specimens within the carrier rack.

With the advent of the inventor's new laboratory automation system as described in co-pending patent application Ser. No. 07/997,281, entitled "METHOD FOR AUTOMATIC TESTING OF LABORATORY SPECIMENS", the inventor has provided a laboratory automation system which requires a different type of specimen carrier. Because the new laboratory automation system of the co-pending patent application calls for identification and conveyance of an individual patient's specimens throughout the laboratory system, it is no longer feasible to utilize conventional specimen tube carrier racks.

Conventional specimen tube carrier racks suffer several drawbacks when considering use in the inventor's new laboratory automation system. First, prior art carrier racks were designed to hold a single type of specimen tube within a rack. Thus, more than one rack would be required for different sizes and types of specimen tubes.

Also, it was not possible to identify the specimen rack and correlate specific test tubes with an individual rack, for independent conveyance throughout a laboratory system.

While the specimen carrier of applicant's co-pending patent application Ser. No. 08/062,785 solved many of these problems, other drawbacks were yet to be addressed. One unaddressed problem was discovered in actual use of the specimen carrier of the applicant's co-pending application. It was found that the weight of a single large test tube at one end of the carrier would be unstable, and liable to fall over while on the conveyor.

Yet another problem of specimen carriers in general was the potential for leakage of fluid in the event of a cracked or broken test tube within the carrier. Spillage of such fluid could easily contaminate the conveyor system as well as persons coming into contact with the specimen carrier.

Finally, conventional specimen carriers were not capable of retaining a specimen slide.

SUMMARY OF THE INVENTION

It is therefore a general object of the present invention to provide an improved specimen carrier for use with a laboratory automation system.

Another object of the present invention is to provide a specimen carrier which will receive a plurality of test tube types in a standardized and uniform arrangement.

Still another object is to provide a specimen carrier with a forward identification surface permitting automated identification of the carrier on a conveyor system.

A further object of the present invention is to provide a specimen carrier which permits individual retention and guidance even when stacked in a line of carriers.

Yet another object is to provide a specimen carrier which is stable, even when holding only a single test tube therein.

Still a further object of the present invention is to provide a specimen carrier which will retain fluids from leaking test tubes in the specimen carrier body.

Still another object is to provide a specimen carrier with the capacity to retain a specimen slide.

These and other objects will be apparent to those skilled in the art.

The specimen carder of the present invention is designed for transporting conventional specimen tubes throughout an automatic laboratory conveyance system. The specimen carrier includes a generally rectilinear carrier body with a forward face having an identification zone delimited thereon. An identification code is marked in the identification zone so as to permit mechanical sensing and identification of the carrier on a conveyor system. A plurality of holes of various diameters and depths are provided in the top surface of the carrier to receive conventional specimen tubes of various types. The deepest holes are located centrally, so that the carrier is stable while retaining specimens therein. Because the carrier is designed for use on an automatic laboratory system, various types of specimen tubes must be disposed within the specimen carrier such that the top end of the specimen tube is located at a predetermined height above the top surface of the carrier. This permits automatic retraction of the specimen tube by other robotic devices. A groove is formed in the top surface of the carrier body which extends between the specimen tube holes, so as to communicate any fluid spilling from a test tube to the other empty holes in the specimen carrier, thereby retaining the fluid within the body of the carrier. A special vertical slot is provided in one of the vertical holes, with a pair of opposing vertical channels, so as to retain a specimen slide in the specimen carrier.

BRIEF DESCRIPTION OF THE DRAWINGS

FIG. 1 is a front perspective view of the specimen carrier of the present invention;

FIG. 2 is an end elevational view of the specimen carrier mounted on a conveyor track;

FIG. 3 is a sectional view taken at lines 3—3 in FIG. 4;

FIG. 4 is an end elevational view taken from the left end of FIG. 1;

DESCRIPTION OF THE PREFERRED EMBODIMENTS

Figure 5:
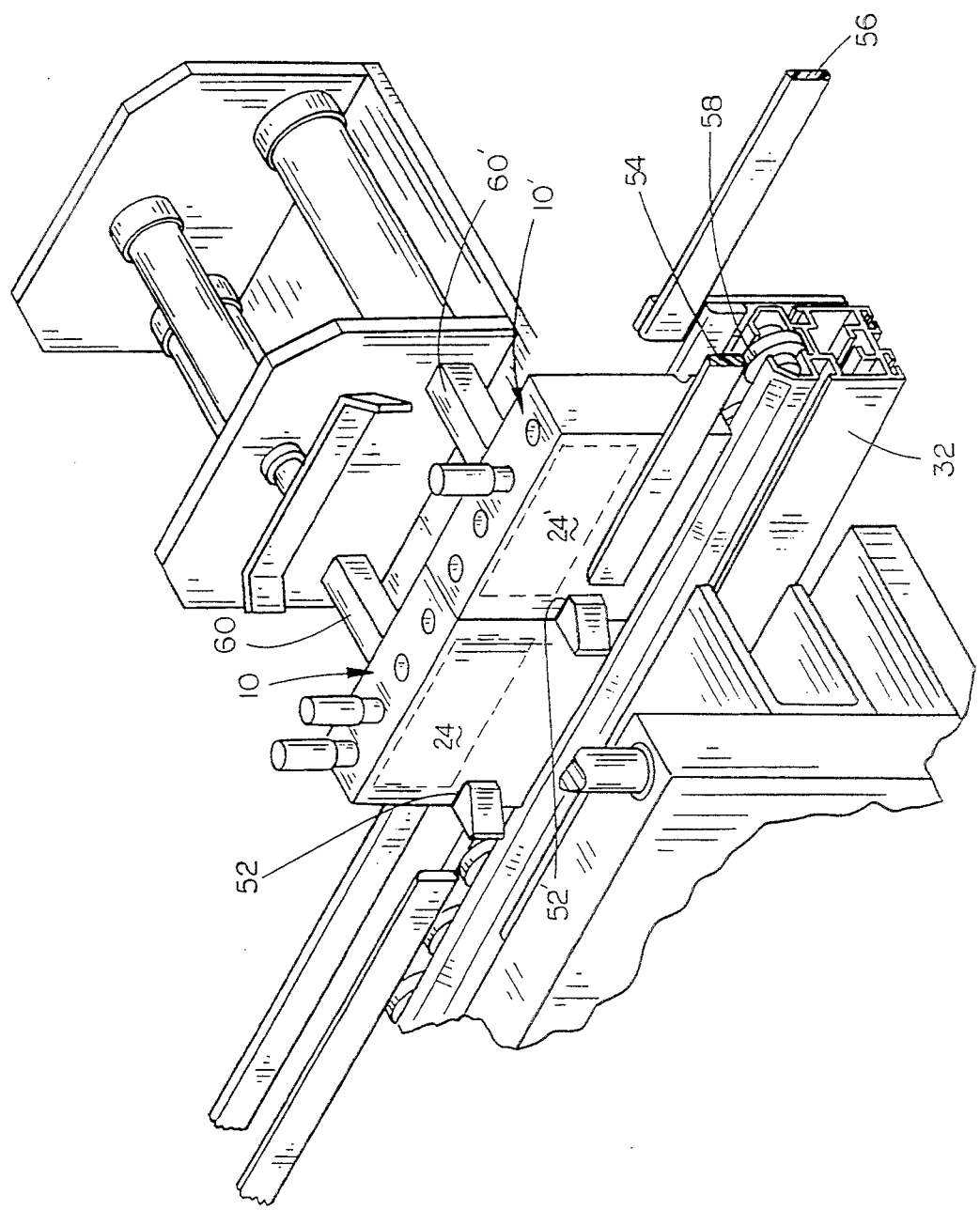
FIG. 5 is a pictorial view of two specimen carriers being transported on an automatic conveyor system.

Referring now to the drawings, in which similar or corresponding parts are identified with the same reference numeral, and more particularly to FIG. 1, the specimen carrier of the present invention is designated generally at 10 and is preferably formed of a solid lightweight block of plastic material. Carrier 10 includes a forward face 12, a rearward face 14, top surface 16, bottom surface 18, and right and left end walls 20 and 22, respectively. Forward face 12 has an identification zone 24 located thereon, on which an identification code 26, shown in FIG. 1 as printed bar code is located. Identification zone 24 has top and bottom boundaries 28a and 28b located a predetermined distance down from top surface 16, and left and right boundaries 30a and 30b located a predetermined distance from left end wall 22 and right end wall 20, respectively. In this way, when a plurality of specimen carriers 10 are aligned on a conveyor track 32, as shown in FIG. 5, a sensor, such as a bar code reader (not shown) can determine the beginning and end of any identification code located within identification zone 24. In addition, bar code 26 may be oriented both horizontally and vertically (as shown), so that a sensor may be conveniently oriented in either direction.

Referring to FIGS. 1 and 3, four holes, 34, 36, 38 and 40 are formed in top surface 16 and extend downwardly towards bottom surface 18 predetermined distances. Preferably, first hole 34 is approximately 7/16 inch in diameter and has a depth of approximately 1.3 inches. Hole 36 is approximately ½ in diameter and has a depth of approximately 2.5 inches. Third hole 38 has a diameter of about ½ inch and a depth of approximately 1.8 inches. Finally, fourth hole 40 has a diameter of about ⅝ inch and a depth of approximately 2.6 inches. The diameters and depths of holes 34–40 are determined for specific types of specimen tubes commonly utilized in the medical field. The varying depths of holes 34–40 are necessary in order to maintain a standard height "H" of the top 42 of test tube 44 above top surface 16 of carrier 10, as shown in FIG. 2. This standard height "H" is particularly critical in automated laboratory systems because the automated functions of various equipment is based upon this standard dimension. For example, a robotic arm utilized to remove a test tube 44 from specimen carrier 10 will be programmed to grip a test tube at a particular location within height "H" to remove the test tube from the carrier. The robotic arm will also rely on the location of the grip on the test tube for relocating the test tube at the particular apparatus utilized to conduct a test on a specimen within the test tube. If the upper end 42 of test tube 44 is not within a predetermined dimension, a robotic arm could easily break the test tube or incorrectly align a test tube within the scientific instrument.

Furthermore, the conveyor system for specimen carriers 10 utilizes standard clearances to permit travel of specimen carriers around the conveyor on track 32. Without a standardized height, it may be difficult or impossible to utilize the specimen carrier 10 on the conveyor system, since the required clearance may not be met.

As discussed above, identification zone 24 provides a space for an ID code to permit an automated laboratory system to identify the specimen carrier and route the carrier throughout the conveyor system as required for the specimens within the carrier. In order to avoid requiring sensors on both sides of the conveyor track 32, specimen carrier 10 is provided with a groove 46 extending horizontally along the rearward face 14 of carrier 10. Groove 46 corresponds with a projecting pin 48 mounted on a rear guide rail support arm 50 at individual work stations. In this way, after the testing of a specimen has been completed, specimen carrier 10 is inserted on track 32 and must move past pin 48 to continue on the conveyor system. If specimen carrier 10 is oriented correctly, groove 46 will permit carrier 10 to move past pin 48. If carrier 10 is reversed, pin 48 will prevent passage of the specimen carrier 10. In this way, forward face 12 of carrier 10 is always directed outwardly to permit sensing by a sensor.

As shown in FIG. 1, identification zone 24 has a lower boundary 28b spaced from top surface 16, and upper, left and right boundaries 28a, 30a and 30b, located relative to top wall 16, left end wall 22 and right end wall 20. Lower boundary 28b is located a distance below top surface, 16 which corresponds to the height of the forward guard rail 54, as shown in FIGS. 2 and 5, so that bar code 26 may be sensed by a sensor located above guard rail 54.

Forward and rearward guard rails 54 and 56, are supported on support arms 50 above the transport surface 58 of track 32. Guard rails 54 and 56 are spaced apart to permit movement of carrier 10 therebetween, and are spaced above transport surface 58 to permit a sensor to scan identification zone 24. Referring now to FIGS. 3 and 4, a generally rectangular notch 52 is formed in left end wall 22. Notch 52 is located so as to receive an extendible arm 60 therethrough, as shown in FIG. 5. The laboratory automation system includes gates and elevators to remove a specimen carrier 10 from the conveyor track 32, to redirect specimen carrier 10 to a secondary track or various work station.

FIG. 5 shows two specimen carriers 10 and 10' retained in a stationary position by extendible arm 60 and a second extendible arm 60'. Notch 52' on carrier 10' permits arm 60' to extend between carriers 10 and 10' to retain specimen carrier 10' in position until carrier 10 is redirected to an appropriate location.

Referring now to FIGS. 3 and 4, a pair of spaced apart apertures 62 and 64 extend vertically upwardly in bottom surface 18. Each aperture 62 and 64 has an annular chamfer 66 and 68 respectively, forming a conical shape into each aperture, for a purpose described in more detail herein below.

Figure 6:
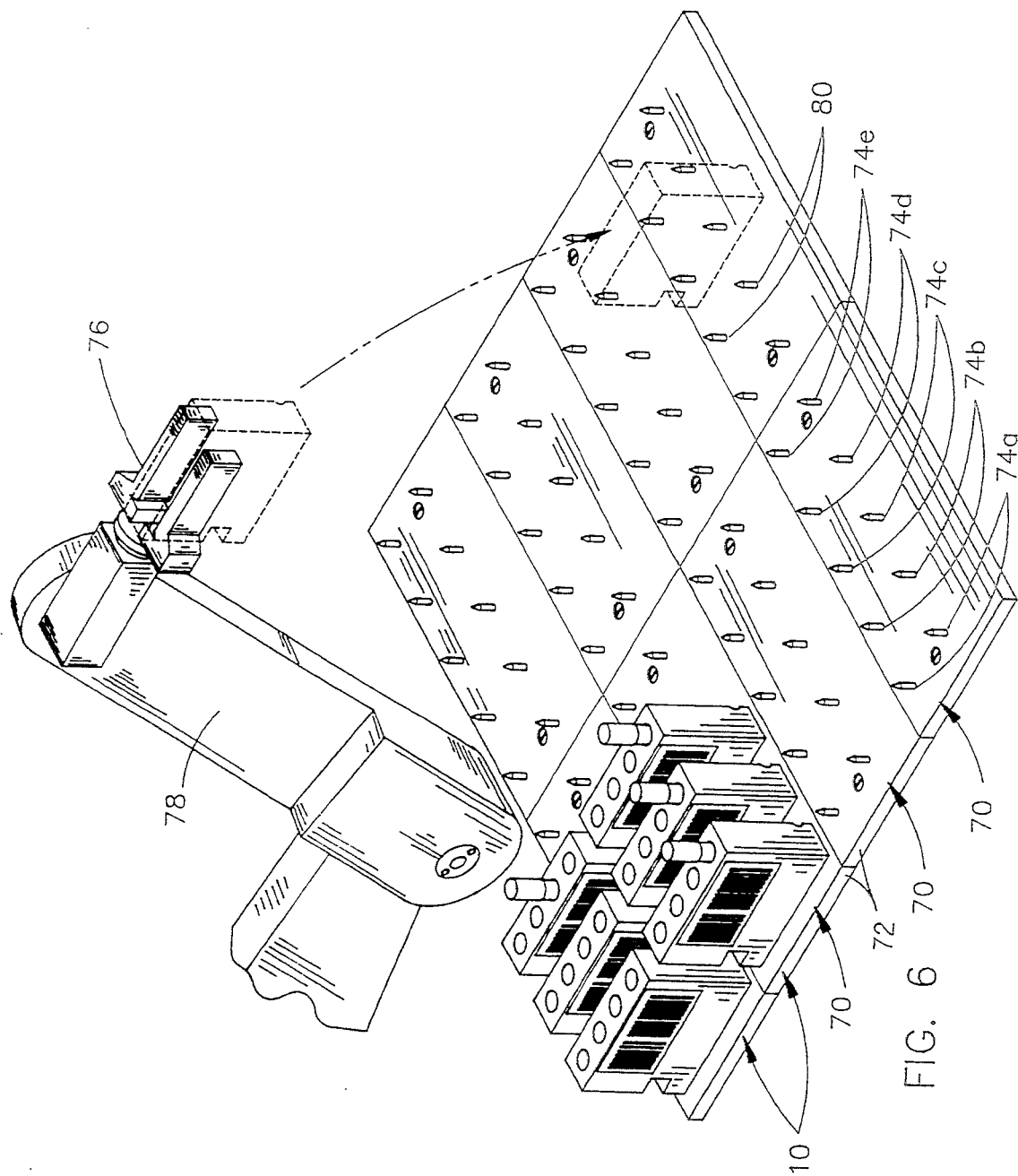
FIG. 6 is a perspective view of specimen carrier storage racks and a robotic arm for placement thereon.

Specimen carrier 10 may be temporarily stored on storage racks 70, as shown in FIG. 6. Each storage rack 70 includes a base plate 72 with a plurality of locator pins 74 projecting upwardly from the upper surface of base plate 72. Locator pins 74 are arranged in sets of pairs 74a, 74b, 74c, 74d and 74e, each set of pins being longitudinally spaced apart so as to correspond with the pair of apertures 62 and 64 (see FIG. 3) on each specimen carrier 10. Pin pairs 74a–74e are spaced apart laterally a distance such that specimen carriers 10 are laterally spaced apart to permit the specimen carrier to be grasped by the jaws 76 of a robot arm 78.

The laboratory automation system for which the specimen carriers 10 are designed includes robot arms at various work stations which will remove a specimen tube from the specimen carrier for further processing. For those work stations which permit processing of more than one specimen tube at a time, it is desirable to locate the individual specimen carriers in a defined position where the robot arm 78 can easily locate the appropriate specimen carrier. While such robotics are very accurate, movement of the specimen carrier from vibration or other external forces, could prevent the robot arm from locating and retrieving the specimen carrier, or from accurately positioning a test tube into the appropriate specimen carrier.

Locator pins 80 are preferably formed with a conical point 80 at their upper end to assist in precisely locating a specimen carrier 10 on the base plates 72. Conical chamfers 66 and 68 formed in apertures 62 and 64, respectively, assist in this placement, so as to direct the specimen carrier 10 on the locator pins, despite minor misalignment of the specimen carrier with the locator pins.

A plurality of storage racks 70 may be mounted on a surface adjacent the robot arm 78 as desired to locate and store specimen carrier 10, as shown in FIG. 6.

Figure 7:
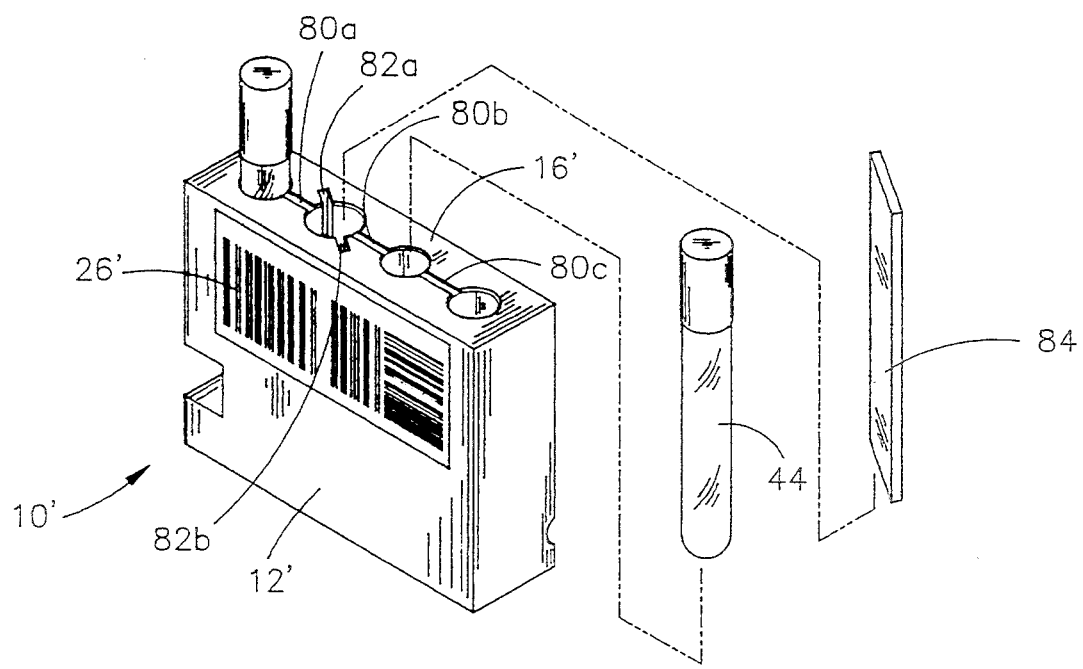
FIG. 7 is a pictorial view of a second embodiment of the specimen carrier.
Figure 8:
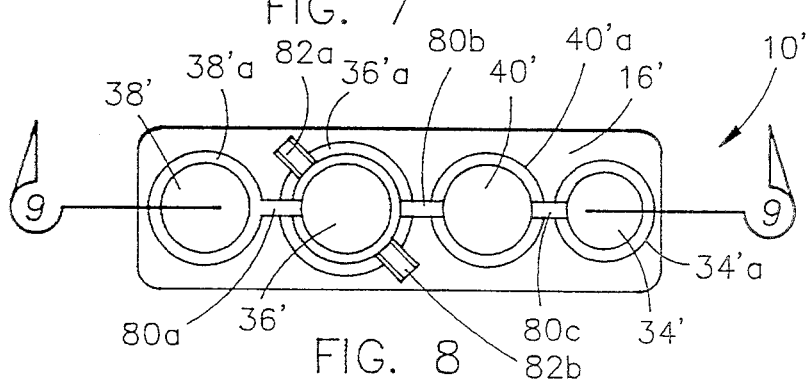
FIG. 8 is a top plan view of the specimen carrier of FIG. 7.
Figure 9:
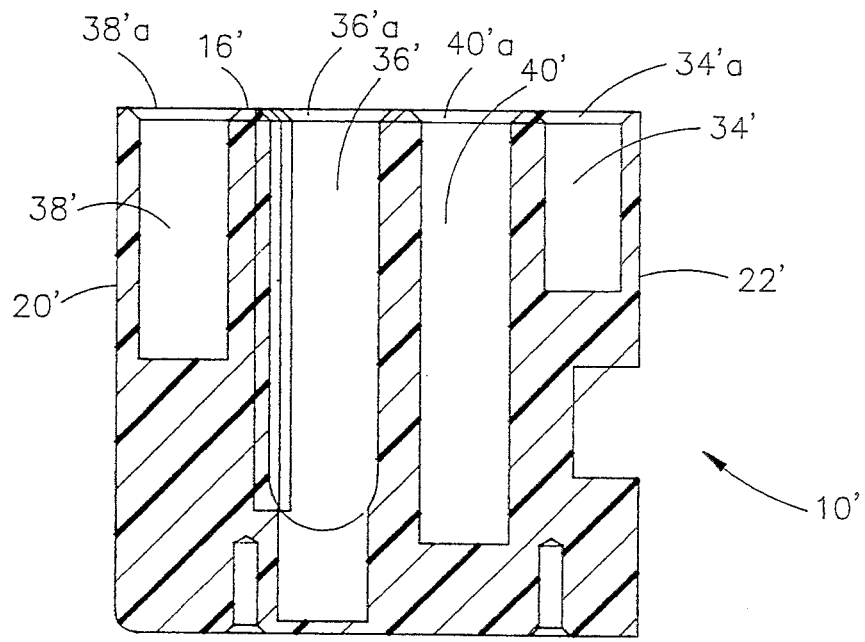
FIG. 9 is a sectional view taken at lines 9—9 in FIG. 8.

Referring now to FIGS. 7–9, a second embodiment of the specimen carrier of the present invention is designated generally at 10' and is substantially the same shape and size as specimen carrier 10 of FIG. 1. Forward face 12' includes an identification code 26' thereon for identifying the specimen and specimen carrier.

As shown in FIG. 9, holes 34', 36', 38' and 40' are rearranged in top surface 16' such that the holes of the greatest depth, 36' and 40', are located centrally, while holes 34' and 38', of lesser depth are located adjacent the end walls 20' and 22'. This orientation of holes 34'–40' stabilizes the specimen carrier when only a single test tube 44 is inserted within specimen carrier 10'.

As shown in FIGS. 8 and 9, each hole 34', 36', 38', and 40' is chamfered at its upper end, forming funnel shaped portions 34'a, 36'a, 38'a and 40'a.

A set of three coaxial grooves 80a, 80b and 80c are formed in top surface 16' so as to connect pairs of holes in specimen carrier 10'. As shown in FIG. 8, groove 80a extends between holes 38' and 36', groove 80b extends between holes 36' and 40', and groove 80c extends between holes 40' and 34'. In this way, a leak in a test tube in one of holes 34'–40' would cause fluid to flow within one of grooves 80a, 80b and 80c into adjoining holes so as to retain all fluid within the specimen carrier body.

Referring now to FIGS. 7 and 8, a pair of diametric, vertical channels 82a and 82b are formed in hole 36', which extend downwardly from top surface 16'. Channels 82a and 82b form the edges of a slot which will receive a conventional specimen slide 84, shown in FIG. 7, in an upright fashion within specimen carrier 10'.

Whereas the invention has been shown and described in connection with the preferred embodiment thereof, it will be understood that many modifications, substitutions and additions may be made which are within the intended broad scope of the appended claims. For example, the number and size of holes within the specimen carrier is determined only by the variety of the specimen tube types that are desired to be utilized in the laboratory automation system. Similarly, while a conventional bar code is shown for the identification code, various other types of identification code materials could be utilized in printed format or otherwise.

Therefore, there has been shown and described an improved specimen carrier which accomplishes at least all of the above stated objects.

I claim:

1. A specimen carrier for transporting a laboratory specimen carried within a specimen tube or a rectangular specimen slide, comprising:
    a carrier body having a forward face and opposing rearward face, a top surface and opposing bottom surface, a right end wall and opposing left end wall;
    specimen tube carrying means on said carrier body for carrying at least one specimen tube in a generally upright position and with an upper end of the specimen tube located at a predetermined height above the top surface of said carrier body; and
    said specimen tube carrying means including a first vertical hole formed in the upper surface of said carrier body having a predetermined diameter and depth so as to receive a predetermined specimen tube partially therein with an upper end located a predetermined distance above the carrier body top surface;
    specimen slide carrying means on said carrier body for carrying at least one specimen slide in a generally vertical position with an upper end of the specimen slide located at a predetermined height above the top surface of said carrier body; and
    said specimen slide carrying means including a pair of opposed, vertically-oriented channels formed diametrically along walls of said first vertical hole.

2. The specimen carrier of claim 1, wherein said specimen carrier tube carrying means includes a second vertical hole formed in the top surface of the carrier body, spaced from the first hole, having a predetermined diameter and depth so as to receive a predetermined specimen tube partially therein with an upper end located a predetermined distance above the carrier body top surface; wherein the first and second holes have different depths to receive different length specimen tubes, and wherein upper ends of specimen tubes located within the first and second hole are located at substantially the same distance above the carrier body top surface.

3. The specimen carrier of claim 1, wherein said channels extend downwardly a predetermined distance so as to receive a predetermined slide therein with a top edge located a predetermined distance above the carrier body top surface.

4. The specimen carrier of claim 1, wherein said first and second holes have different depths to receive different length specimen tubes with top ends of the specimen tubes located at substantially the same distance above the carrier body top surface.

5. The specimen carrier of claim 4, further comprising a third vertical hole formed in the top surface of the carrier body, spaced from the first and second holes, having a predetermined diameter and depth so as to receive a predetermined specimen to be partially therein, said third hole having a different depth than said first and second holes to receive a predetermined specimen tube with a top end located at substantially the same distance above the carrier body top surface as specimen tubes in the first and second holes, and wherein the hole having the greatest depth is located intermediate the other two holes and generally centrally between the ends of the carrier body.

6. A specimen carrier for transporting a laboratory specimen carried within a specimen tube, comprising:

a carrier body having a forward face and opposing rearward face, a top surface and opposing bottom surface, a right end wall and opposing left end wall; and a first vertical hole formed in the top surface of said carrier body having a predetermined diameter and depth so as to receive a predetermined specimen tube partially therein;

a second vertical hole formed in the top surface of the carrier body, spaced from the first hole, having a predetermined diameter and depth so as to receive a predetermined specimen tube partially therein;

said first and second holes being enclosed from the top surface to their full depths, to retain fluid therein; and a groove formed in the top surface of the carrier body and extending between said first and second holes to cause fluid within one hole to flow to the other hole without leaving the body of the carrier.

7. The specimen carrier of claim 6, wherein the top surface is chamfered around each hole, and said groove extends between the chamfered portions of the holes.

* * * * *